United States Patent [19]
Worden et al.

[11] Patent Number: 5,846,829
[45] Date of Patent: Dec. 8, 1998

[54] METHOD AND APPARATUS FOR GROWING PLANT CELLS

[75] Inventors: Robert Mark Worden, Holt; Kenneth C. Sink, Okemos; Tyler T. Ames, Lansing, all of Mich.; Vicki S. Thompson, Idaho Falls, Id.

[73] Assignee: Board of Trustees operating Michigan State University, East Lansing, Mich.

[21] Appl. No.: 748,508

[22] Filed: Nov. 8, 1996

[51] Int. Cl.⁶ .................... C12N 5/02; C12N 5/04
[52] U.S. Cl. .................. 435/420; 435/426; 210/695; 210/807
[58] Field of Search ................. 210/661, 695, 210/807; 435/420, 426

[56] References Cited

U.S. PATENT DOCUMENTS

| | | | |
|---|---|---|---|
| 4,828,492 | 5/1989 | Agnone | 433/173 |
| 5,626,764 | 5/1997 | Burns et al. | 210/661 |

OTHER PUBLICATIONS

Bramble, J. L. et al. Biotechnol. Prog 6:452–457, 1990.
Graham et al. Mol. Plt–Microb. Interacta 3(3):157–66, 1990.
Kudou et al. Agric. Biol. Chem. 55(9):2227–2233, 1991.
Gansborg, O.L. et al. Exp. Cell Res. 50: 151–158, 1968.
Vieth, W., Gene expression with plant cells. In Bioprocess engineering: kinetics, mass transport reactors and gene expression, John Wiley & Sons: New York, 265–324 (1994).
Phyton Gesellschaft fur Biotechnik mbH)(Dornenburg, H., et al., Enzyme and Microbial Technology 17:674–684 (1995).
Shuler, M., et al., Bioreactor consid. for producing flavors and pigments . . . In Biotechnology and food process eng.: Schwartzberg, H., Rao, M., Eds: Marcel Dekker: NY, pp. 45–65 (1990).
Ten Hoopen, H., et al., Possibilities, problems and pitfalls . . . In Progress in plant cellular and molecular biology: Nijkamp, H.: Van der Plas, L., Van Aartrijk, J. Eds: Kluwer Academic Publishers: Boston, 673–681 (1990).

Shai, O., et al., Biotechnology Progress 1:1–9 (1985).
Christou, P., Euphytica 74:164–185 (1994).
Jende–Strid, B., Hereditas 119:187–204 (1993).
Yun, D., Proc. Natl. Acad. Sci. USA 89:11799–11803 (1992).
Waugh, R., et al., Plant Genetic Engineering 1–37 (1991).
Mol., J., et al., Use of genetic engineering to improve . . . In Progress in plant cellular . . . Nijkamp, H.; Van der Plas, L; Van Aartrijk, J Eds; Kluwer Academic Publishers: Boston 712–716 (1990).
Uchimiya, H., et al., Journal of Biotechnology 12:1–20 (1989).
Gulik, W., Biotechnology Progress 10:335–339 (1994).
Reinhard, E. et al., Biotechnology and Bioengineering 34:502–508 (1989).
Panda, A., et al., Enzyme Microb. Technol. 11:386–397 (1989).
McKelvey, S., et al., Biotechnology Progress 9:317–322 (1993).
Brodelius, P., Transport and accumulation . . . In Progress in plant cellular and molecular biology; Nijkamp, H.; Van der Plas, L.; Van Aartrijk, J. Eds: Kluwer Acad. Pub. Boston:567–576 (1990).
Graham, T., et al., Mol. Plant–Microbe Interact. 3:157–166 (1990).

(List continued on next page.)

*Primary Examiner*—Toni R. Scheiner
*Attorney, Agent, or Firm*—Ian C. McLeod

[57] ABSTRACT

A method and bioreactor (10) apparatus is described for growing plant cells, particularly to produce plant derived chemicals is described. Bioparticles (11) containing magnetically susceptible particles are provided in a column (12) surrounded by a solenoids (13, 14, 14A) which act to hold the bioparticles in position in the column. One of the solenoids with a magnetically susceptible screen (24) acts as a valve to allow a portion of the bioparticles to be removed from the column. The method is particularly described for producing daidzein and genistein.

15 Claims, 5 Drawing Sheets

OTHER PUBLICATIONS

Kudou, S., et al., Agric. Biol. Chem. 55:2227–2233 (1991).
Barz, W., et al., Phenolic Metabolism in Plants 139–165 (1992).
Rosensweig, R., Science 204:57–60 (1979).
Rosensweig, R., et al., AIChE Symposium Series 77:8 (1981).
Siegell, Powder Technology 39:215–222 (1984).
Jaraiz–M., et al. AIChE 30:951–966 (1984).
Siegell, J., Powder Technology 55:127–132 (1988).
Liu, Y., et al., Power Technology 64:3–41 (1991).
Weng, D., et al., AIChE Symposium Series on Fluidized Processes 289:107–115 (1992).
Hu, T., et al., Chem. Eng. Res. Des. 65:238–242 (1987).
Bramble, J., et al., Biotechnology Progress 6:452–457 (1990).
Leckie, F., et al., Effect of bioreactor design and agitator speed on the growth and alkaloid accum. by cultures of Catharanthus roseus 13:296–305 (1991).
Facchini, P., et al., Biotech. Bioeng. 37:397–403 (1991).
Zhong, J., et., Biotech. Bioeng. 38:653–658 (1991).
Dorgelo, E., et al., Chem. Eng. Sci. 40:2105–2111 (1985).
Akiyama, T., et al., J. Biol. Chem. 262:5592–5595 (1987).
Mueller, S., et al., J. Cell Biol. 119:1309–1325 (1992).
Yanagihara, K., et al., Cancer Res. 53:5815–5821 (1993).
Jing, Y., et al., Anticancer Res. 15:1147–1152 (1995).
Watanabe, T., et al., Cancer Research 51:764–768 (1991).
Jing, Y., et al., Anticancer Res. 13:1049–1054 (1993).
Scholar, E., et al., Cancer Lett, 87:159–162 (1994).
Rosenshine, I., et al., Infection and Immunity 60:2211–2217 (1992).
Okura, A., et al., Biochem. Biophysical Research 157:183–189 (1988).
Fotsis, T., et al., 90:2690–2694 (1993).
Yang, W., et al., Ind. Eng. Chem. Process Des. Dev. 21:717–721 (1982).
Fett, W., and R. Zacharius, Plant Sci. Lett 24:303–309 (1982).
Gamborg, O., et al., Experimental Cell Res. 50:151–158 (1968).
Westrin, B., and A. Axelsson, Biotech. and Bioeng. 38:439–446 (1991).
Ananta, M., et al., Biotech. Bioeng. 47:541–549 (1995).
Pollock, K., et al., Plant Cell Reports 2:36–39 (1983).
Brown, D., et al., Plant Cell Tissue Organ Culture 1:165–180 (1982).

METHOD AND APPARATUS FOR GROWING PLANT CELLS

SUMMARY OF THE INVENTION

(1) Field of the Invention

The present invention relates to a process for growing plant cells, particularly to produce chemicals either intracellularly or extracellularly in a magnetofluidized bed bioreactor apparatus. The apparatus uses a magnetic valve to allow sequential removal of a portion of bioparticles from a column after a pre-selected residence time in the bioreactor.

(2) Description of Related Art

Many plant secondary metabolites have value as pharmaceuticals, food colors, flavors and fragrances. Plant pharmaceuticals include for instance: taxol, genistein, diadzein, codeine, morphine, quinine, shikonin, ajmalacine, and serpentine. Food product examples are anthocyanins, saffron, vanilla, and a wide variety of other fruit and vegetable flavors and texture modifying agents. Production of biochemicals from higher plants is attractive where compounds do not naturally occur in microbial or mammalian systems, or where compounds are produced by polygenic (multiple gene) processes not amenable to gene transfer (Vieth, W., Gene expression with plant cells. In Bioprocess engineering: kinetics, mass transport, reactors and gene expression. John Wiley & Sons: New York, 265–324 (1994)). The exploitation of plant production of biochemicals has been largely limited, however, to whole plant systems. While at least 30 compounds are known to accumulate in plant cell culture at concentrations equal or greater than in whole plants, literature reports of commercial production are limited to shikonin from *Lithospermum erythrorhizon* and taxol and other products from Taxus (Phyton Gesellschaft für Biotechnik mbH) (Dörnenburg, H., et al., Enzyme and Microbial Technology 17:674–684 (1995)). Plant cell culture offers several potential advantages over harvest and extraction of whole plants. Continuous production, rather than seasonal, is possible in a bioreactor where conditions can be controlled for optimal product formation. Plant cell culture can provide a high quality, uniform product while reducing labor costs (Shuler, M., et al., Bioreactor considerations for producing flavors and pigments from plant tissue culture. In Biotechnology and food process engineering; Scwartzberg, H., Rao, M., Eds; Marcel Dekker: New York, pp. 45–65 (1990)) and eliminating the effects of weather and disease.

Industrial application of plant cell culture has been limited by a number of drawbacks including slow growth rates, low product yields, intracellular storage of product, and poorly understood metabolic regulation. Perhaps the largest roadblock to industrial application of plant cell culture is low productivity per volume (Ten Hoopen, H., et al., Possibilities, problems and pitfalls of large-scale plant cell cultures. In Progress in plant cellular and molecular biology; Nijkamp, H.; Van der Plas, L.; Van Aartrijk, J. Eds; Kluwer Academic publishers: Boston, 673–681 (1990)). Production of shikonin is an example where this has been overcome however. High-yield cell lines obtained by repeated selection had a shikonin content 25 times that of the original strain (Sahai, O., et al., Biotechnology Progress 1:1–9 (1985)). In addition to isolation of high yield cell lines, genetic manipulation may enable dramatic increases in product yields. Progress in understanding of biochemical pathways and genetic engineering of plants has been reported for several systems (Dörnenburg, H., et al., Enzyme and Microbial Technology 17:674–684 (1995); Christou, P., Euphytica 74:164–185 (1994); Vieth, W., Gene expression with plant cells. In Bioprocess engineering: kinetics, mass transport, reactors and gene expression. John Wiley & Sons: New York, 265–324 (1994); Jende-Strid, B., Hereditas 119:187–204 (1993); Yun, D., Proc. Natl. Acad. Sci. USA 89:11799–11803 (1992); Waugh, R., et al., Plant Genetic Engineering, 1–37 (1991); Mol, J., et al., Use of genetic engineering to improve yields in cell cultures, e.g. (anti) sense DNA technology. In Progress in plant cellular and molecular biology; Nijkamp, H.; Van der Plas, L.; Van Aartrijk, J. Eds; Kluwer Academic publishers: Boston 712–716 (1990); Uchimiya, H., et al., Journal of Biotechnology 12:1–20 (1989)). Application of this knowledge base is likely to create new opportunities for production of plant cell biochemicals. As metabolic barriers to commercially interesting yields are overcome, other barriers to plant cell culture should simultaneously be addressed such as bioreactor design. Experiments need to be performed at an early stage in the type of reactor to be used at large scale, as growth and production rates may change completely with reactor type (Ten Hoopen, H. et al., Possibilities, problems, and pitfalls of large-scale plant cell cultures. In Progress in plant cellular and molecular biology; Nijkamp, H.; Van der Plas, L.; Van Aartrijk, J. Eds; Kluwer Academic publishers: Boston 673–681 (1990)).

Several reactor schemes are available for plant cell cultures, including stirred tanks, bubble columns, air-lift reactors, hollow-fiber membranes, liquid-dispersed trickle and incline reactors, and mist bioreactors for hairy root culture (Gulik, W., Biotechnology progress 10:335–339 (1994); Reinhard, E., et al., Biotechnology and Bioengineering 34:502–508 (1989); Panda, A., et al., Enzyme Microb. Technol. 11:386–397 (1989); McKelvey, S. et al., Biotechnol. Prog. 9:317–322 (1993)). However, each of these reactors has limitations, such as cell death from shear, insufficient mixing at high cell densities, settling of cells, and difficulty in scale-up (Panda, A., et al., Enzyme Microb. Technol. 11:386–397 (1989)). Furthermore, many of these reactors are poorly suited for a continuous operation in which the product is accumulated intracellularly.

Immobilization offers several advantages for using plant cells. Cell densities may reach 110 g/L in alginate beads, while suspension culture is limited to about 30 g/L (Sahai, O., et al., Biotechnology Progress 1:1–9 (1985)). The close proximity of immobilized cells allows intercellular communication and transport that can be important for differentiation and secondary-metabolite production (Shuler et al., 1990). Attachment and plugging caused by free cells are eliminated by immobilization (Sahai, O., Biotechnology Progress 1:1–9 (1985)).

Fluidized bed bioreactors are well suited for immobilized cell systems. Low shear forces and pressure drops prevent damage to fragile cells. Excellent contact between the gas, liquid, and solid phases eliminates the need for mechanical mixing.

An important disadvantage of conventional immobilized cell systems, however, is that plant secondary metabolites are typically stored intracellularly (Brodelius, P., Transport and accumulation of secondary metabolites. In Progress in plant cellular and molecular biology; Nijkamp, H.; Van der Plas, L.; Van Aartrijk, J. Eds; Kluwer Academic Publishers: Boston, 567–576 (1990)). Soybean isoflavonoids, as an example, exist predominantly as glucoside-malonylated conjugates (Graham, T., et al., Mol. Plant-Microbe Interact. 3:157–166 (1990); Kudou, S., et al., Agric. Biol. Chem. 55:2227–2233 (1991) which are located in the vacuole (Barz, W., et al., Phenolic Metabolism in Plants, 139–165

(1992). Permeabilization methods for release of products into the media results in low culture viability. Brodelius (Brodelius, P., In Progress in plant cellular and molecular biology, 567–576 (1990)) notes that it appears very difficult, if not impossible, to release vacuolar substances into the medium by permeabilization of the plasma membrane and the tonoplast without killing the cells.

A magnetofluidized bed (MFB) consists of a fluidized bed of magnetically susceptible particles to which a direct-current (DC) magnetic field is applied. The magnetic field induces dipoles in the particles that cause the particles to align along the field lines, thus eliminating the solids mixing that occurs in unstabilized fluidized beds. However, like conventional fluidized beds, the magnetized solids can still be passed through the bed. Continuous solids throughput without mixing (i.e. "plug flow") is possible (Rosensweig, R., Science 204:57–60 (1979); Rosensweig, R., et al., AIChE Symposium Series 77:8 (1981); Siegell, Powder Technology 39:215–222 (1984), Jaraiz-M., et al. AiChE 30:951–966 (1984); Siegell, J., Powder Technology 55:127–132 (1988)). Applications for MFBs have been reviewed by Liu, Y., et al., Power Technology 64:3–41 (1991)) including bioreactors for continuous ethanol fermentation (Weng, D., et al., AIChE Symposium Series on Fluidized Processes 289:107–115 (1992)) and phenol degradation (Hu, T., et al., Chem. Eng. Res. Des. 65:238–242 (1987)). Bramble et al. (Bramble, J., et al., Biotechnology Progress 6:452–457 (1990)) operated a magnetofluidized bed in batch mode with plant cells (*Coffea arabica*). However, none of these bioreactors were operated in a solids-throughput mode.

The primary advantage of the MFB bioreactor is that it allows continuous processing of the bioparticles with tight control of their residence time in the reactor. A maximum in product concentration with respect to time has been observed for a variety of plant systems, including *Glycine max* (Shuler, M., Ann. N. Y. Acad. Sci. 65–79 (1981)), *Catharanthus roseus* (Leckie, F., et al., Effect of bioreactor design and agitator speed on the growth and alkaloid accumulation by cultures of *Catharanthus roseus* 13:296–305 (1991)), *Thalictrum rugosum* (Facchini, P., et al., Biotech. Bioeng. 37:397–403 (1991)), and *Perilla frutescens* (Zhong, J., et al., Biotech. Bioeng. 38:653–658 (1991)). In a MFB, the optimal residence time for product concentration can be used. In contrast, a conventional fluidized bed with a three-week average residence time, a typical axial dispersion coefficient of 4 $cm^2/s$ (Dorgelo, E., et al., Chem. Eng. Sci. 40:2105–2111 (1985)), and a bioreactor length of 60 cm, has a Peclet number of $5\times10^{-5}$. The residence time distribution corresponding to this value is that of a stirred tank (Fogler, H., Elements of Chemical Reaction Engineering. Prentice-Hall: New Jersey (1986)), indicating that the bioparticle would be well mixed. The average product concentration would thus be lower than that of the MFB due to some product bioparticle having residence times shorter than the optimum and some longer. Additional advantages and disadvantages of MFB bioreactors have been discussed by Bramble (Brambles J., et al. Biotechnology progress 6:452–457 (1990)).

Protein tyrosine kinases (PTKs) play a key role in cancer induction, proliferation, and metastasis (Akiyama, T., et al., J. Biol. Chem. 262:5592–5595 (1987); Mueller, S., et al., J. Cell Biol. 119:1309–1325 (1992); Mustelin, T., et al., TIBS 215–220 (June, 1993)). Genistein, a potent inhibitor of PTKs, has been shown to have antiprolific effects on human hepatocarcinoma (Mousavi, Y., et al., Steroids 58:301–304 (1993)) and stomach cancer cells (Yanagihara, K., et al., Cancer Res. 53:5815–5821 (1993)). Genistein and daidzein can induce Erythroleukemia cells to differentiate into non-cancerous cells (Jing, Y, et al., Anticancer Res. 15:1147–1152 (1995); Watanabe, T., et al., Cancer Research 51:764–768 (1991)). Daidzein was also found to have potent differentiation-inducing activity for human leukemia cells, both in vitro and in vivo (Jing, Y., et al., Anticancer Res. 13:1049–1054 (1993)). Genistein has also been shown to block the invasion by tumor cells (Scholar, E., et al., Cancer Lett, 87:159–162 (1994)) and block bacterial uptake by epithelial cells (Rosenshine, I., et al., Infection and Immunity 60:2211–2217 (1992)). Topoisomerase is involved in several steps necessary for cell proliferation, including breaking DNA for replication, transcription, recombination, and integration. Genistein limits the ability of ras oncogenes to transform cells by inhibiting topoisomerase, and this inhibition was found to occur only in transformed cells (Okura, A., et al., Biochem. Biophysical Research 157:183–189 (1988)). Genistein was found to inhibit angiogenesis of endothelial cells in vitro as well as proliferation of several types of cancer (neuroblastoma, rhabdyosarcoma, and Ewings Sarcoma) (Fotsis, T., et al., 90:2690–2694 (1993)).

There is a need for an improved magnetofluidized bed reactor apparatus and method.

OBJECTS

It is therefore an object of the present invention to provide a novel magnetofluidized bed reactor apparatus and method. Further, it is an object of the present invention to provide a method and apparatus which is reliable and economical. These and other objects will become increasingly apparent by reference to the following description and the drawings.

DESCRIPTION OF DRAWINGS

FIG. 4A is a dark-field image of bead with soybean aggregates appearing as lighter regions; FIG. 4B shows the same bead under transmission illumination with soybean appearing as darker regions in center, and stainless steel preventing passage of light around edges; FIG. 4C shows a different bead with three dark regions of soybean, illustrating larger aggregate sizes.

DESCRIPTION OF PREFERRED EMBODIMENTS

Figure 1:
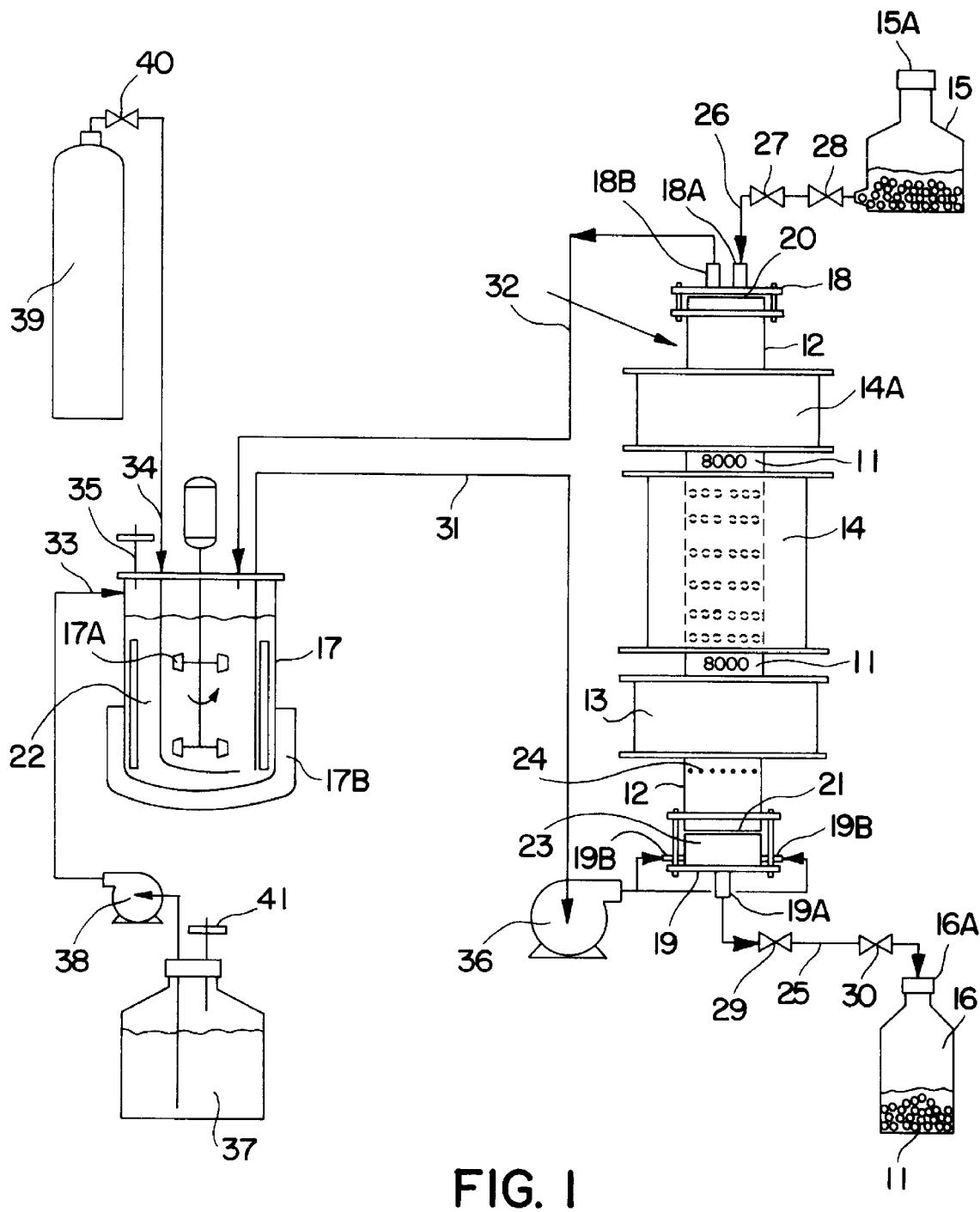
FIG. 1 is a front view of the magnetofluidized bed bioreactor 10 particularly useful for continuous production of isoflavonoids from soybean.
Figure 1A:
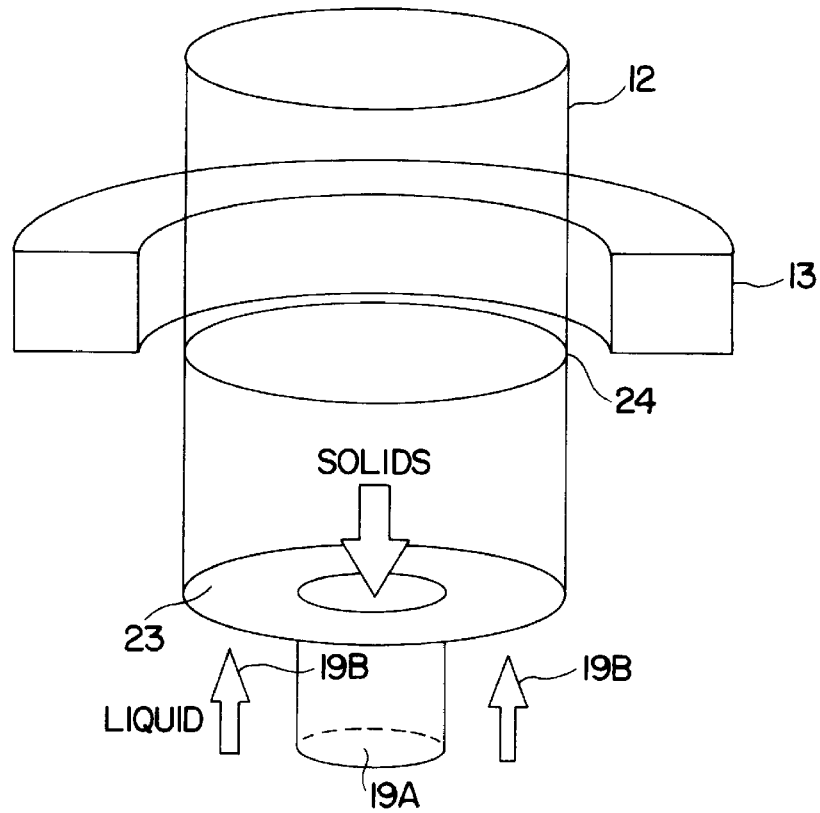
FIG. 1A is a perspective schematic partial cross-sectional view of the column 12, solenoid 13, and screen 24 forming the magnetic valve as shown in FIG. 1.
Figure 1B:
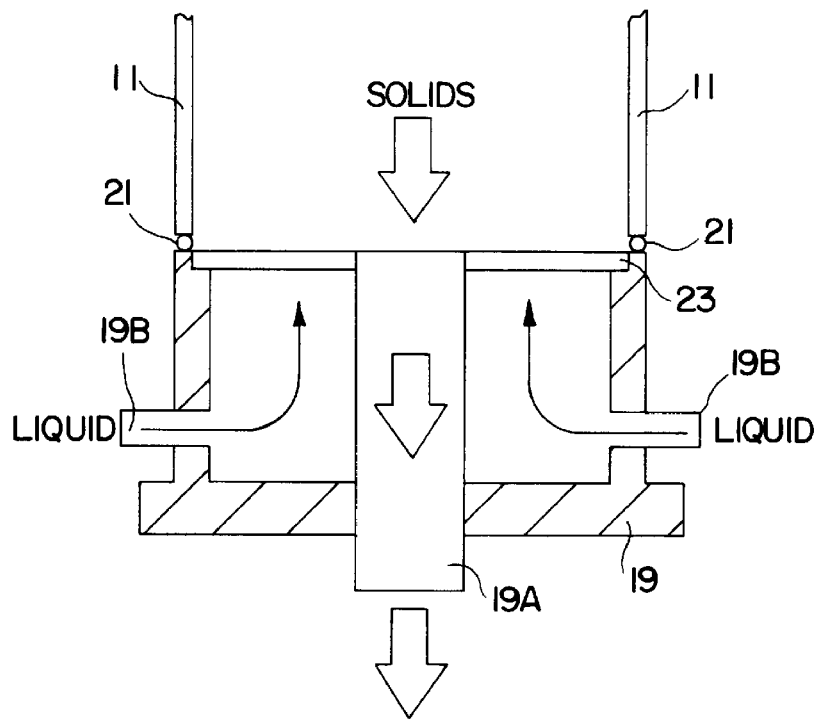
FIG. 1B is a front cross-sectional view of the base end plate 19 as shown in FIG. 1 showing the mesh 23 and o-ring 21.
Figure 1C:
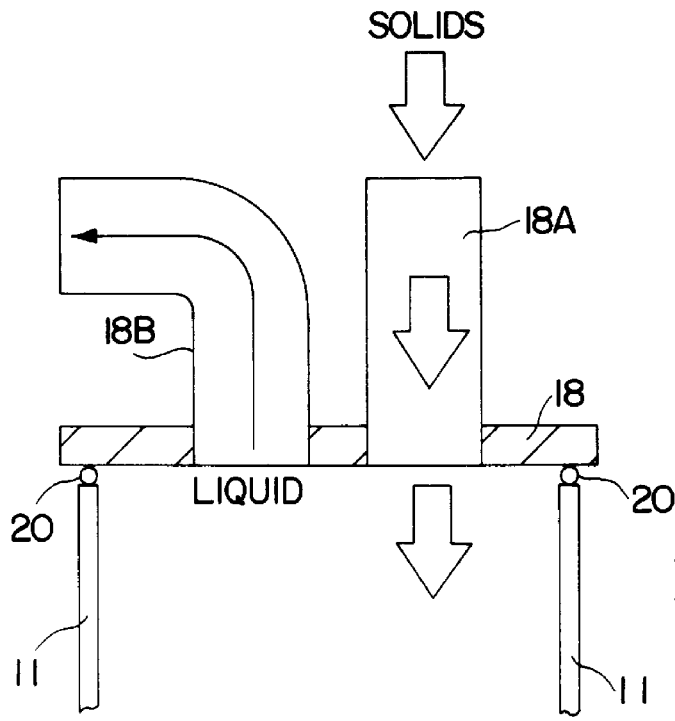
FIG. 1C is a front cross-sectional view of the head end plate 18 as shown in FIG. 1.

The present invention relates to a process for growing plant cells in a culture medium and removing the cells from the culture medium, the improvement which comprises:

(a) providing bioparticles, formed by binding the cells of the plant material and magnetically susceptible particles together, in a column with opposed ends for inlet and outlet of bioparticles and with an activated first electromagnetic field generator around the column between the end which produces a magnetic field which holds the bioparticles in position in a portion of the column without mixing of the bioparticles in the column and with an activated second electromagnetic field generator around the column acting with a magnetically susceptible screen across the column to prevent bioparticles from being moved from the portion of the column between the first electromagnetic field generator and the outlet;

(b) circulating a culture medium for the cells through the bioparticles as they are held in position by the activated electromagnet; and (c) repeatedly adding bioparticles at one part of the column; and (d) removing bioparticles from another part separated from the one part of the column by inactivating the second electromagnetic field generator wherein a portion of the bioparticles are removed from the magnetic field.

Further, the present invention relates to an improved apparatus for growing plant cells in a culture medium and for removing the cells from the culture medium which comprises:

(a) a column with opposed ends for inlet and outlet of bioparticles containing cells of the plant material, wherein the plant material is bound to magnetically susceptible particles to form the bioparticle;

(b) a first electromagnetic field generator mounted around the column between the ends which produces a magnetic field which holds the bioparticles in position in the column;

(c) a second electromagnetic field generator around the column between the first electromagnetic field generator and the outlet; and (d) magnetically susceptible screen mounted across the column which when activated acts with the second electromagnetic field generator to prevent the bioparticles from being removed from the column and when inactivated allows a portion of the bioparticles to pass through the screen with the first electromagnetic field generator activated.

The plant cells which can be grown in the reactor of the present invention are numerous. Included in the definition of "plant cells" are cells with a rigid supporting cell structure. The products which can be recovered from the plant cells are as varied as the plants. The cells have to be able to be grown in a culture medium.

The "culture medium" is as varied as the cells. Typically the culture medium includes carbon and nitrogen sources, trace nutrients, salts, and hormones.

Gels, such as alginate and carrageenan and agar are preferred to bind the magnetically susceptible particles to the plant cells. Other binders such as adhesives and the like can be used.

The magnetically susceptible particles are preferably stainless steel. Other particles are for instance, iron and magnetite. The amount used is preferably between 1 and 50 percent by weight.

Continuous bioparticle throughput eliminates the need for metabolite release. Fresh cells can be continually added at the reactor, maintained in the reactor for the optimal length of time, and then removed for product recovery. The solids residence time would be chosen to optimize the intracellular product concentration, and controlled by the rate of solids throughput. Continuous operation also minimizes bioreactor down time, and thus offers increased productivity over batch operation.

Isoflavonoids constitute an important class of 15-carbon phenolic compounds sharing a similar carbon skeleton. Found in all plant tissues, isoflavonoids have been shown to exhibit a wide range of biochemical activities. In the Examples, continuous production of two key isoflavonoids, daidzein and genistein, from soybean (*Glycine max*) cell culture. These compounds have important medical applications. The following is an Example of the present invention.

EXAMPLE

A magnetofluidized bed (MFB) bioreactor 10 was used for continuous production of daidzein and genistein from immobilized soybean culture for over 2 months. The MFB bioreator 10, which offers continuous, plug-flow bioparticle 11 throughput, is well suited for production of intracellularly stored plant metabolites. Soybean cultures were co-immobilized with ferritic stainless steel in calcium alginate spheres. Transport of bioparticle 11 through a column 12 was controlled with a magnetic valve solenoid 13. Immobilized soybean concentrations reached over 10 g dry tissue per L of bioparticle. The average and maximum specific growth rates in the MFB (0.07 and 0.17 $day^{-1}$) were nearly one-third and two-thirds of batch shake flask culture specific growth rates respectively. Daidzein and genistein concentrations ranged from 10 to 200 $\mu$g per gram of dry soybean tissue. Bioparticle microscopy and Thiele modulus calculations suggested that oxygen diffusion in the bioparticle was not rate limiting. Ampicillin, Timentin, and Benlate were found to have limited phytotoxicity at concentrations useful in preventing contamination in long-term, continuous bioreactor 10 operation.

The goal of this Example was to achieve continuous production of plant secondary metabolites in the MFB bioreactor 10 with continuous bioparticle 11 throughput. Specifically daidzein and genistein were produced from soybean via continuous solids processing for over 60 days without contamination. Supporting research included batch shake flask experiments to study the effect of immobilization on growth, and to determine suitable concentrations of antimicrobial agents. Finally, the degree to which oxygen diffusion within the bioparticle 11 was rate limiting to soybean growth was assessed.

Materials and Methods

Chemicals. All chemicals for soybean cell culture medium were purchased from Sigma Chemical (St. Louis, Mo.) except sucrose from J. T. Baker (Phillipsburg, N.J.). LB medium was purchased from Gibco (Paisley, Scotland). Sodium alginate and genistein were purchased from Sigma Chemical. Stainless steel powder (grade 410-L) was purchased from Alfa Aesar (Ward Hill, Mass.). Daidzein was purchased from ICN Biomedicals (Aurora, Ohio). Ampicillin and gentamicin were purchased from Sigma Chemical, and Timentin was purchased from SmithKline Beecham (Philadelphia, Pa.). Benlate was supplied by DuPont (Wilmington, Del.). Helium was purchased from AGA Gas (Cleveland, Ohio). Acetonitrile, ethyl acetate, and acetic acid were purchased from EM Science (Gibbstown, N.J.). All other chemicals were purchased from J. T. Baker.

Equipment. The MFB bioreactor 10 used in this work is illustrated in FIGS. 1, 1A, 1B and 1C. The main components of the MFB bioreactor 10 are the fluidized bed of the bioparticle 11, solenoids 13 and 14 and 14A, bioparticle reservoirs 15 and 16, and mixing vessel 17. The column 12 was 60 cm long and 5 cm in diameter and made of Pyrex glass with grooved ends for O-rings 20 and 21. Custom machined stainless steel endplates 18 and 19 were sealed with the O-rings 20 and 21. The head endplate 18 had a port 18A for solids inlet and a port 18B for liquid outlet. The base endplate 19 had a center outlet port 19A for solids and an annular region for liquid inlet through inlet port 19B. The annular region of column 12 was fitted with a stainless steel fluidization mesh 23 (Michigan Dynamics, Heathrow, Fla.) which provided liquid distribution.

The solenoid 13 together with the screen 24 functioned as a magnetic valve for solids (MVS) and was used to control bioparticle flow from the MFB bioreactor 10. The MVS solenoid 13 consisted of a magnetic coil surrounding column 12 in the vicinity of a magnetically susceptible screen 24. The screen 24 openings are large enough to allow free passage of bioparticle 11 when no current is applied to the solenoid 13. Supplying power to the solenoid 14 results in an induced magnetic field at the screen 24 that stops solids flow. Details of MVS construction and operation are given by Jaraiz-M. et al. (Jaraiz-M., et al., Powder Technol. 38:53–61 (1984)) and Yang et al. (Yang, W., et al., Ind. Eng. Chem. Process Des. Dev. 21:717–721 (1982)). The magnetic valve screen 24, which consisted of a 430 stainless steel wire mesh 4×4 (Belleville Wire Cloth, Cedar Grove, N.J.), was fixed to the glass with silicone sealant near the bottom of the column 12. An axial, DC magnetic field was supplied by the three solenoids 13, 14 and 14A designed to provide an approximately even field strength over the total length of the solenoids. The solenoid 13 also provided the magnetic field for the magnetic valve for solids. Power for the solenoids 13, 14 and 14A was supplied by a Kepco (Flushing, N.Y.) DC power supply (ATE 100-5M) rated at 100 volts and 5 A.

The feed bioparticle reservoir 15 was a 2 L aspiration vessel sealed with a foam stopper 15A covered with aluminum foil and connected by tubing 26. A Wheaton solvent flask with a modified screw cap 16A served as the product bioparticle reservoir 16. Bioparticle outlet tubing 25 passed through the cap 16A via a hole that was sealed with silicone sealant. Both reservoirs 15 and 16 were connected to their respective headplates 18 and 19 with the tubing 25 and 26 (silicone). Clear tubing (1.5 cm ID) allowed visualization of bioparticle movement as it was controlled with pinch clamps 27, 28, 29 and 30. The mixing vessel 17 was a Bioflo II (New Brunswick, Edison, N.J.) fermentation system with a 1.5 L vessel. The Bioflo II system provided agitation via stirrer 17A, temperature control via jacket 17B, and dissolved oxygen monitoring. Connections to the vessel included a suction line 31 to the base endplate 19 of the column, a return line 32 from the head endplate 18 of the column 12, a fresh medium inlet 33, a sparging gas inlet 34, and a head space vent. All tubing was norprene or silicone. Liquid was pumped to the column 12 with a high capacity Masterflex peristaltic pump 36 (Cole Parmer, Chicago). Liquid returned from the column 12 by gravity. A 20 L reservoir 37 provided fresh medium via a peristaltic pump 38 (Cole Parmer) as needed and was provided with a vent 41. An oxygen cylinder 39 regulated at 5 psi was connected to the vessel sparge inlet 34. The gas flow rate was controlled by a peristaltic pump 40 (Cole Parmer).

HPLC. Isoflavonoid analysis was conducted using high performance liquid chromatography (HPLC). A Waters (Milford, Mass.) 600 multisolvent pump, Waters 490 multiwavelength UV absorbance detector, Waters system interface module, and a PC for data acquisition and processing comprised the system. A 25 cm by 4.6 mm Rainin (Woburn, Mass.) Microsorb-MV column containing 5 $\mu$m C-18 packing was used. A refillable 3 cm guard column with pellicular C-18 packing (Alltech, Deerfield, Ill.) was used to protect the analytical column.

Gas Chromatography. Gas chromatography of the MFB gas phase was performed on a Perkin Elmer (Norwalk, Conn.) Autosystem Gas Chromatograph with a thermal conductivity detector. Fixed gases were separated on a 9.1 m by 2.2 mm Hayesep DB 100/120 SS column (Alltech) with helium as the mobile phase. A Perkin Elmer 600 Series Link and PC were used for data acquisition and instrument control.

Plant Culture and Analysis. Suspension cultures were maintained on a Lab-Line (Melrose Park, Ill.) 3590 Orbital Shaker. All culture transfer and immobilization was conducted in a sterile laminar flow hood (Baker Company, Sanford, Me.). A Stir Pak lab stirrer (Cole Parmer) and a Teflon microcentrifuge sample pestle (Fisher, Pittsburgh) were used for extraction of isoflavonoids. Samples were centrifuged in an Eppendorf 5415C centrifuge (Brinkmann Instruments, Westbury, N.Y.). A Cenco drying oven (Central Scientific, Chicago) was used for dry weight analysis. All sterilization was performed in a Amsco (Farmington, Mich.) steam autoclave at 121° C. A Reichert Microstar IV microscope (Cambridge Instruments, Buffalo, N.Y.) was used for light microscopy of bioparticle. A Pulnix TM-7CN CCD camera (Sunnyvale, Calif.) was used for image capture. Image data were acquired using Quanta (Mountain View, Calif.) WinVisionPro software on a PC.

Respiration. Dissolved oxygen was measured with an Ingold $O_2$ sensor (12 mm diameter) and an Ingold Model 170 oxygen amplifier (Mettler-Toledo, Wilmington, Mass.). Data were acquired with a PC, DT2801 analog and digital I/O board (Data Translation, Marlboro, Mass.), and Labtech Notebook software (Laboratory Technologies, Wilmington, Mass.). For suspension culture, the oxygen sensor was inserted into a 100 mL graduated cylinder via a rubber stopper. For immobilized soybean, a miniature packed bed system was assembled using a 15 cm by 2.5 cm ID Pyrex column. Column ends were plugged by rubber stoppers which were connected via Tygon tubing (Cole Parmer). The bottom stopper was fitted with a metal screen to prevent passage of bioparticle. The oxygen sensor entered the column through the top stopper. Liquid was circulated with a Masterflex peristaltic pump (Cole Parmer).

Soybean Culture. Suspension cultures of *Glycine max* cv. Mandarin were initiated according to Fett and Zacharius (Fett, W., and R. Zacharius, Plant Sci. Lett 24:303–309 (1982)). Suspension cultures were maintained at 25°–27° C. on a rotary shaker at 125 rpm. They were subcultured by passing two-week old cultures through a 400 $\mu$m sieve. Twenty mL of this inoculum was added to 50 mL of fresh B5 medium (Gamborg, O., et al., Experimental Cell Research 50:151–158 (1968)) with 1.0 mg/L 2,4-D and 0.15 mg/L kinetin (1-B5 medium). All transfers were conducted in a laminar flow hood.

Figure 6:
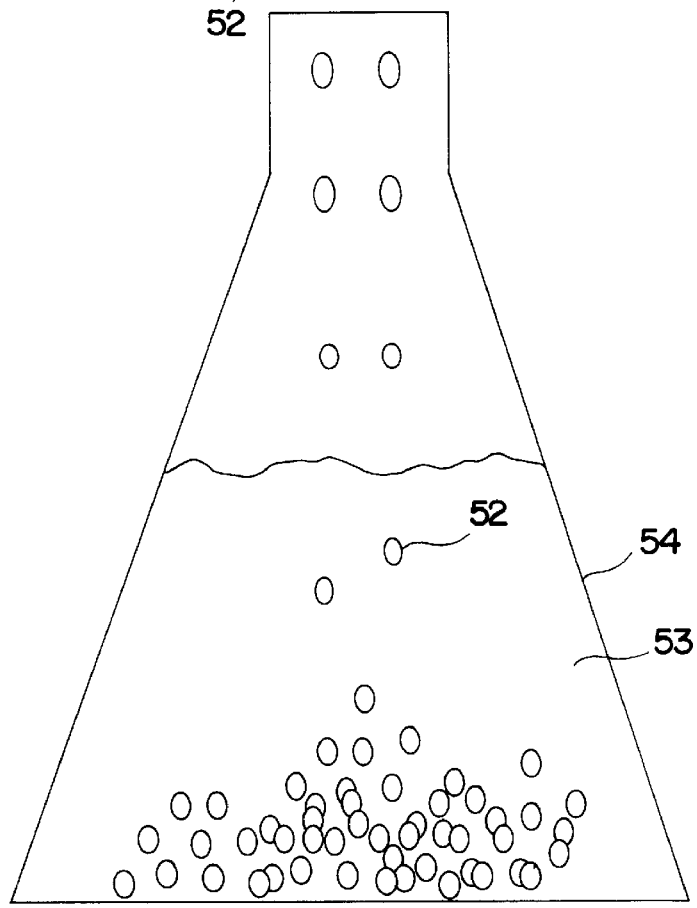
FIG. 6 is a schematic front cross-sectional view of the preferred apparatus for making the bioparticles.
Figure 6A:
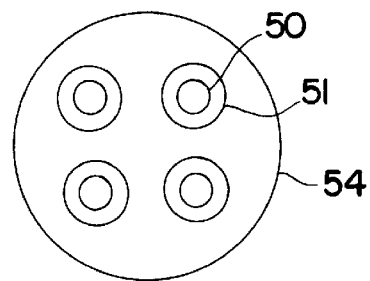
FIG. 6A is a cross-section along line A—A of FIG. 6.

Immobilization. Immobilization solution (150 mL aliquots) consisting of 2% medium viscosity sodium alginate and 25% (w/w) stainless steel particles was prepared and autoclaved in 500 mL Erlenmeyer flasks. A soybean inoculum was prepared by passing an approximately 2 week old culture through a 1 mm sieve. The filtrate was added to the immobilization solution and peristaltically pumped through a sterile bead-making apparatus into hardening solution. As shown in FIGS. 6 and 6A, the bead-making apparatus consisted of feed tubing leading to four 16 gauge syringe needles 50 with flattened tips 50A. Each needle 50 was fitted with concentric tubing 51 to provide a shearing stream of sterile filtered air A that decreased bead 52 size. Beads 52 were approximately 2 mm in diameter. Hardening solution 53 (400 mL) in container 54 consisted of 0.1M calcium chloride and 20 g/L sucrose. After 20 minutes, the hardening solution was decanted and replaced with 200 mL of 1-B5 medium. For MFB use, antibiotics/antimycotics were added (50 mg/L ampicillin, 100 mg/L Timentin, and 25 mg/L Benlate). Before addition to the MFB bioreactor 10, each batch of fresh bioparticle 11 was sampled (approximately 10 mL) with a sterile 25 mL wide-mouth pipette for dry weight analysis. The entire process was conducted in a laminar flow hood. See Smidsrod, O., et al., Tibtech 71–77 (1990) and Brodelius, P., Cell Culture and Somatic Cell (Academic Press 535–547 (1984)) for further information on forming the bioparticle 11.

Cell Recovery. Bioparticle 11 volume was measured by volume displacement in a 50 mL graduated cylinder. Sample volumes were approximately 10 and 20 mL for feed and product samples respectively. Samples were placed in 125 mL Erlenmeyer flasks with approximately 50 mL of 0.2M sodium citrate to dissolve the alginate matrix. Flasks were placed on a rotary shaker for 30 minutes at 300 rpm. Suspended cell mass was decanted while stainless steel was retained by placing a magnet on the bottom of the flask. Complete recovery of cell mass was achieved by removing the magnet, adding deionized water to wash the stainless steel, and decanting suspended cell mass with the magnet on the bottom of the flask.

Analytical Procedures. Dry Weight. Decanted cell mass was collected by filtering through dried and tared Whatmann 41 ashless filter paper using a glass microanalysis filter holder (Fisher, Pittsburgh, Pa.). Samples were dried overnight at 70° C. and weighed. Samples immobilized with stainless steel were then ashed in tared, ceramic crucibles over a Bunsen burner, cooled in a desiccator, and weighed. The ash in the crucible was taken as the mass of residual stainless steel which was not separated from the soybean tissue.

Bioparticle Microscopy. Product bioparticle was sliced to obtain a cross-section from the center of the particle. The cross-sections were examined at 40 times magnification for distribution of cell mass. Both transmission and dark-field illumination were utilized. Images were acquired by mounting a CCD camera on the microscope.

Extraction of Isoflavonoids. Soybean tissue recovered from product bioparticle 11 was extracted by the following method adapted from Graham (Graham, T., et al., Plant Physiol. 95:584–593 (1991)). Product bioparticle 11 was stored frozen until used. Approximately 0.200 g of soybean tissue was extracted twice with 0.400 mL of 80% ethanol (20% water) in a 1.5 mL microfuge tube by grinding with a Teflon microfuge pestle for 5 minutes. Previous testing verified a greater than 95% average recovery of the isoflavonoids using this extraction protocol. The combined extracts were injected directly into the HPLC after centrifugation. Following HPLC analysis of the extracts, a portion of each sample was subjected to a hydrolysis treatment to liberate daidzein and genistein from sugar moiety compounds. In a screw-top test tube, 0.400 mL of sample was combined with 4 mL of 1N HCl and put in a 100° C. water bath for 1 hour. The hydrolysis mixture was then extracted with 1 mL of ethyl acetate. The ethyl acetate extract was dried at 40° C. in a microfuge tube and dissolved in 0.400 mL methanol (ethyl acetate adversely affected chromatograms). The hydrolyzed extracts were analyzed by HPLC in the same manner as raw extracts.

Isoflavonoid Analysis. HPLC analysis was performed with gradient programming. Mobile phase A was acetonitrile with 0.5% acetic acid and mobile phase B was water with 0.5% acetic acid. Adjustment of pH with acetic acid significantly reduced band tailing. The gradient linearly increased from 30% A to 45% A over 20 minutes, followed by a 2 minute linear increase to 90% A, a 10 minute hold, and a 5 minute linear return to 30% A. Retention times were 8.0 and 14.9 minutes for daidzein and genistein respectively. UV absorbance was monitored at 254 nm.

Identities of daidzein and genistein where verified by sample spiking and mass spectrometry. Retention times of daidzein and genistein in the sample matrix were checked by adding standards to soybean extracts. Fractions of the HPLC effluent were collected and analyzed by electrospray mass spectrometry in negative ion mode (M-1). Daidzein and genistein were verified by peaks at 253 and 269 amu, respectively.

Respiration. For suspension culture, the entire contents of a 250 mL shake-flask culture were put into the graduated cylinder along with fresh medium to approximately 100 mL total volume. The liquid was then sparged with air for 5 minutes. The oxygen sensor was inserted with care to remove any head space, and the stirring speed was set to give complete mixing in the cylinder. Dissolved oxygen concentration data were collected until a steady value was reached.

For immobilized culture, the apparatus described above was filled with product bioparticle. The oxygen sensor was inserted, and the remaining volume was filled with deionized water. The pump speed was set to keep the liquid well mixed.

Batch Shake Flask Cultures. Shake flask cultures were conducted to study the effects of immobilization on soybean growth. The study compared suspension culture, cells immobilized in alginate, and cells immobilized in alginate with 25% (w/w) stainless steel. Replicate cultures in 1 L Erlenmeyer flasks contained 400 mL of 1-B5 medium. Suspension cultures had 30 mL of inoculum while immobilized cultures had 20 mL of inoculum in approximately 200 mL of beads. A common inoculum was used for all flasks to reduce error due to soybean variation. Immobilization followed the procedure described above. Cultures were maintained on an orbital shaker at 125 rpm.

Shake flask cultures were also conducted to study the effects of antimicrobial agents on soybean growth. Effects of ampicillin (100 mg/L), gentamicin (50 mg/L), Timentin (200 mg/L), and Benlate (50 mg/L) were studied in 1 L Erlenmeyer flasks containing 400 mL of 1-B5 medium. A common inoculum (30 mL) was used for all flasks, including two controls.

MFB Bioreactor 10 Operation. Start-up. As the entire MFB bioreactor 10 system was designed to fit into an autoclave, system connections made after autoclaving were minimized. Only the two connections to the column head endplate 18 were made post-autoclaving as necessitated by mounting of the solenoids 13, 14 and 14A. The fresh medium reservoir 37 was also filled prior to autoclaving and did not contain antibiotics/antimycotics. After mounting and final connections were made, the column 12 was filled with the medium 22 from reservoir 17 and liquid circulation started. The liquid flow rate was set to approximately 1.6 L/min. Ampicillin, Timentin, and Benlate were added to the circulating medium yielding 50, 100, and 25 mg/L concentrations respectively. The solenoids 13, 14 and 14A power supply was set at 2 A, yielding a magnetic field strength of 150–180 gauss depending on position in the column 12. The column 12 was loaded with immobilized soybean bioparticle 11 (feed bioparticle) in four aliquots over the first three days of operation. Agitation in the Bioflo reservoir 17 was set at 250 rpm. Sparging with air from oxygen cylinder 39 was not started until the dissolved oxygen concentration dropped below 80% of the initial value.

Continuous Bioparticle Processing. At intervals varying from one to several days, product bioparticle 11 was removed from the bottom at outlet 19A of endplate 19 of the column 12, and feed bioparticle 11 was added to the top at the inlet 18A through endplate 18. Intervals during the first 12 days were chosen with the goal of demonstrating growth during that period. From day 12 through 34, scheduling obligations resulted in irregular bioparticle 11 addition/removal. Past day 34, bioparticle 11 was exchanged roughly every four days. To minimize bed mixing, the liquid flow rate was reduced to 1 L/min before bioparticle 11 removal operations. The power supply to the solenoids 13, 14 and 14A was increased to 3 A. The upper clamp 29 of two pinch clamps 29 and 30 on the outlet tubing 25 was opened slightly to allow the length of tubing 25A between the upper and lower pinch clamps to fill with medium 22 from the column 12. At the same time, air was displaced into the column 12. Once the tubing was filled with liquid, the upper clamp 29 was completely removed. The power supply to the solenoids 13, 14 and 14A was then reduced to 0.6 A, yielding a magnetic field strength of 40 gauss at the magnetic valve 24. Bioparticle 11 was induced to fall through the screen 24 by squeezing the outlet tubing 25. No mixing in the remaining bioparticle 11 bed was observed due to the stabilization afforded by the 50–60 gauss magnetic field in the column. After the desired quantity of bioparticle 11 had passed through the screen 24, the solenoid power was returned to 3 A. While the greater portion of the released bioparticle 11 fell through the outlet hole 19A in the base endplate 19, the remainder which came to rest on the fluidization mesh 23 was removed by briefly increasing the liquid flow rate to 3 L/min. Once all the bioparticle 11 was in the outlet tubing 25, the liquid flow rate was returned to 1.6 L/min. The bottom clamp 30 was then removed, releasing the bioparticle 11 into the product reservoir 16. The bottom clamp 30 was replaced, and the process repeated once more, resulting in 150–200 mL of bioparticle in the reservoir. Following bioparticle 11 removal, additional medium was drained into the product reservoir 16 making room for addition of fresh medium 22. The solenoid power was returned to 2.0 A. The final step in removal was an aseptic exchange of the full bioparticle reservoir 16 with an empty one.

After product bioparticle 11 was removed, feed bioparticle 11 was added using a similar pinch-clamp 27 and 28 technique. Freshly prepared bioparticle 11 and medium 37 were added to the feed bioparticle reservoir. The upper of two pinch clamps 27 and 28 was removed allowing fresh liquid medium 22 and bioparticle 11 to fill the inlet tubing. Repeated squeezing of the tubing 26 facilitated movement of bioparticles 11 from the reservoir 15 to the tubing 26, displacing the liquid. Once the tubing 26 was full of bioparticle 11, the top pinch clamp 28 was replaced and the bottom pinch clamp 27 removed allowing the bioparticle to enter the column through the head endplate 18. The bottom clamp 27 was replaced and the process repeated until all bioparticle 11 was removed from the reservoir (4–5 times). Fresh medium was then added (approximately 200 mL) by releasing the pinch clamps 27 and 28. The pinch clamps 27 and 28 were then replaced, completing the removal/addition process.

Aseptic conditions during continuous operation were verified by periodically inoculating a rich medium 22 (LB broth) with MFB medium from the product reservoir 16. Both LB agar in petri dishes and LB medium in 125 mL Erlenmeyer shake flask cultures were employed. Shake flasks were incubated at room temperature while petri dishes were incubated at both room temperature and 30° C. for a minimum of two weeks.

Theoretical. Presaturation of the Liquid Phase. Oxygen was dissolved in the liquid phase in the mixing vessel 17 before the medium entered the column 12. An estimate of dissolved oxygen depletion across the column 12 was made using the simple model described below. For steady-state and no mass transfer resistance between the phases, the dissolved oxygen concentration (C) is a function of vertical distance (z) as described by $$v_z \frac{dC}{dz} = - \frac{1-\epsilon}{\epsilon} Q$$

where $v_t$ is the liquid velocity in the z direction, Q is the volumetric oxygen consumption rate in the solid phase, and $\epsilon$ is the void fraction in the column. For operation at 1.6 L/min and an assumed void fraction of 0.4, $v_t$ is 3.5 cm/s. For integration, the height of bioparticle 11 was approximately 40 cm, and the bulk oxygen concentration at 25° C. was taken to be 8.43 mg/L (Bailey, J., and D. Ollis, Biochemical engineering fundamentals. McGraw-Hill: New York (1986)).

Specific Growth Rates. Growth rates during continuous operation were estimated from residence times and cell densities in the feed and product bioparticle. For exponential growth, the average specific growth rate ($\mu$) is described by $$\mu = \frac{\ln\left(\frac{X}{X_0}\right)}{\tau}$$

where $\tau$ is the bioparticle residence time, and X and $X_0$ are the soybean concentrations in the product and feed bioparticle, respectively. Residence times were calculated from the known volumes and times of bioparticle 11 addition and removal, assuming plug flow of the solid phase. Uncertainty in residence times stems from error in measurement of bioparticle 11 volume added and removed as well as any mixing which may have occurred in the column 12. As error in residence time calculations may lead to erroneous pairing of X and $X_0$ values, feed bioparticle cell densities ($X_0$) were taken as the averaged value over the entire run.

Thiele Modulus Calculations. The possibility of oxygen diffusion within the bioparticle limiting the overall reaction rate was assessed with Thiele modulus calculations. An observable modulus ($\Phi$) has been described by Bailey and Ollis (Bailey, J., and D. Ollis, Biochemical engineering fundamentals. McGraw-Hill: New York (1986)) for Michaelis-Menten kinetics which does not require knowledge-of intrinsic-rate parameters:

$$\Phi = \frac{v_0}{D_s S_0} \left( \frac{V_p}{A_p} \right)^2$$

where $v_0$ is the observed volumetric reaction rate, $D_S$ is the diffusion coefficient of substrate in the bioparticle, $S_0$ is the bulk substrate concentration, $V_p$ is the bioparticle 11 volume, and $A_p$ is the bioparticle 11 surface area. For observable modulus calculations, immobilized-soybean respiration rates were measured as described above. Volume and area parameters assumed a 2 mm diameter sphere. An oxygen diffusion coefficient of $1.91 \times 10^{-5}$ cm$^2$/sec was calculated by multiplying the diffusion coefficient in water at 25° C. (Perry, R., et al., Perry's Chemical Engineers' Handbook, 6th Edition. McGraw-Hill: New York (1984)) by correction factors of 0.85 for 2% calcium alginate gel (Westrin, B., and A. Axelsson, Biotech. and Bioeng. 38:439–446 (1991)) and 0.9 for 25% w/w magnetite (Thompson, V., Characterization of a Three-Phase Magnetically stabilized Fluidized Bed Bioreactor, Ph.D. Thesis, Michigan State University, East Lansing, Mich. (1993)). The second correction factor assumes the effects of magnetite and stainless steel at 25% w/w on the effective diffusion coefficient to be equal. The bulk oxygen concentration at 25° C. was taken to be 8.43 mg/L (Bailey, J. and D. Ollis, Biochemical engineering fundamentals. McGraw-Hill: New York (1986)).

The possibility of oxygen diffusion limitations within individual soybean aggregates was assessed with the generalized modulus:

$$\phi = \frac{V_p}{A_p} \sqrt{\frac{n+1}{2} \frac{k_v C_s^{n-1}}{D_e}}$$

where $k_v$ is the intrinsic rate constant, $C_s$ is the bulk substrate concentration, $D_e$ is the effective diffusivity, and n is the reaction order (Froment, G., et al., chemical Reactor Analysis and Design. John Wiley & Sons: New York (1979)). The intrinsic respiration rate was assumed to be that of suspension cultures, and measured as described above. The effective diffusivity was taken as 2% of the value for oxygen in water (Ananta, M., et al., Biotech. Bioeng. 47:541–549 (1995)). Respiration rates measured on a mass basis were translated to a volumetric basis assuming a cell density of 1.02 g/mL (Ananta, M., et al., Biotech. Bioeng. 47:541–549 (1995)) and a dry weight to fresh weight ratio of 0.07 g/g.

Results and Discussion

Batch Shake Flask Cultures. Immobilization. Batch shake flask cultures indicated immobilization slows soybean growth. However, all cultures exhibited exponential growth with $R^2$ values ranging from 0.977 to 0.999 for fitted exponential curves. Specific growth rates for suspension (control), alginate immobilized, and alginate/stainless steel immobilized cultures were 0.35±0.01, 0.21±0.08, and 0.26±0.06 day$^{-1}$ respectively. Immobilization with stainless steel particles reduced the growth rate by about 25% compared to suspension culture. However, the addition of stainless steel particles in the immobilization matrix did not further hinder growth compared to alginate only. While the average specific growth for stainless steel bioparticle 11 cultures was higher than for alginate only, the results cannot be distinguished at the 95% confidence level.

Three aspects of the immobilization protocol merit discussion. First, this work used ferritic stainless steel particles, a novel material for creating a magnetically susceptible bioparticle 11, in place of magnetite. The stainless steel particles chosen for this work offers several advantages over magnetite including a higher magnetic permeability, inherent biological inertness, and easier separation from dissolved immobilization matrix due to increased particle size and density. Stainless steel concentrations employed in this study were much higher than magnetite concentrations reported previously (Bramble, J., et al., Biotechnology Progress 6:452–457 (1990)), and considered realistic for stable bed operation with continuous solids throughput.

Second, the use of concentric air streams to shear immobilization matrix droplets from needles 50 was valuable in maintaining a small bioparticle diameter. The use of concentric, shearing air reduced bead diameters by roughly 50%. Smaller diameters reduce diffusional mass transfer limitations. The minimum size is limited, however, by the relatively large size of suspension culture aggregates. In order to utilize the majority of a 2 week old culture for inoculum, a 1 mm screen was used. This mesh size sets the minimum practical needle 50 size at about 16 gauge.

Third, experimental evidence suggests that stainless steel particles became entrapped within soybean aggregates as they grew. While separating soybean tissue released from the alginate matrix from stainless steel, some soybean aggregates appeared to be drawn to the magnet. Tissue resting on the side of a flask could be moved with a magnet. It was unclear however, if the movement was due to entrapped metal or the presence of metal around the aggregates. Examination at 100 times magnification showed steel particles on or in the aggregates. Again, a clear distinction could not be made. Finally, complete separation of soybean tissue and stainless steel particles was not achieved following dissolution of the alginate, as determined by washing of dry weight samples. Due to the density of stainless steel, it was necessary to account for the mass of steel when determining cell dry weights.

Antimicrobial Agents. Table 1 lists the antibiotic-antimycotic compounds tested, concentrations used and resulting specific growth rates. Of the four agents tested, three were found to have limited toxicity at concentrations useful in inhibiting microbial growth. Only gentamicin was found to be completely toxic to plant cells at the tested concentration. The remaining compounds offer a broad spectrum cocktail to prevent contamination during extended, continuous bioreactor 10 operation. Ampicillin is a broad range antibiotic effective mainly against Gram positive bacteria (Pollock, K., et al., Plant Cell Reports 2:36–39 (1983)). Timentin contains ticarcillin, effective against Gram positive and negative bacteria, as well as clavulanic acid, an anti-betalactamase. Timentin therefore bolsters the stability of ampicillin. Benlate is a broad spectrum antifungal agent (Brown, D., et al., Plant Cell Tissue Organ Culture 1:165–180 (1982)).

Asepsis Testing. Trial runs of the MFB bioreactor 10 were conducted to verify aseptic operation. Initially, the column 12 and endplates 18 and 19 were partially filled with LB medium, sealed, and autoclaved. No microbial growth was apparent after 8 days at room temperature. The complete MFB bioreactor 10 was then tested including liquid circulation and air sparging using LB medium. Asepsis was verified by plating of medium on LB agar after 4 and 6 days of operation. A final trial run was made to verify that bioparticle 11 could be added and removed from the bioreactor 10 aseptically. Alginate beads containing 25% stainless steel were added/removed four times over 24 days without contamination as verified by LB plating of the medium. No antimicrobial agents were used in asepsis testing.

Figure 2:
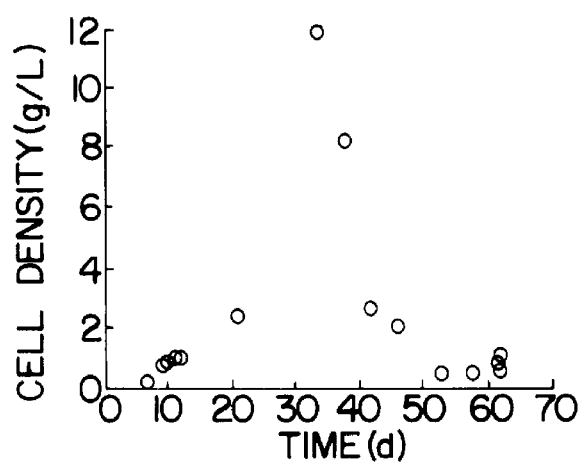
FIG. 2 is a graph showing product bioparticle soybean loading during MFB operation as dry weight per bioparticle volume as a function of time in days (d).

Continuous Operation. Soybean Growth. Continuous operation of the MFB bioreactor 10 utilizing immobilized soybean culture was accomplished during a 62 day run. No evidence of contamination was seen on LB petri dishes or shake flasks. The product bioparticle 11 loadings are shown as a function of time in FIG. 2. Over the first two weeks, the goal of operation was demonstration of soybean growth in the MFB bioreactor 10. Residence times were therefore kept short, and process monitoring was limited to product bioparticle cell densities and dissolved oxygen concentrations. FIG. 2 shows that cell densities increased over the first 12 days, in part due to increasing residence times during start-up. The limited oxygen demand was met by sparging the liquid each day until the dissolved oxygen level returned to the air saturation level.

Following start-up was a period of irregular bioparticle addition/removal. During this time, residence times were increased, and additional monitoring methods were developed. Daily (periodic) sparging was replaced with continuous, peristaltic-pump 40 addition of oxygen to the Bioflo vessel to match the increased oxygen uptake. As seen in FIG. 2, only two product bioparticle 11 aliquots were removed between days 12 and 34. Soybean concentration in the product bioparticle 11 peaked at day 34. The significant decrease in growth after day 34 is likely explained by two experimental problems that are described below.

On day 30, agitation by stirrer 17 in the Bioflo vessel 17 ceased due to bearing failure. Gas-liquid mass transfer was therefore hindered for the remainder of the experiment. Within three days after agitation ceased, dissolved oxygen levels dropped considerably below air saturation levels. An effort to counter decreasing oxygen levels was made by gradually increasing oxygen feed to the Bioflo vessel 17. However, dissolved oxygen levels continued to drop through day 45 while head space analysis indicated oxygen levels well above ambient conditions (results not shown). During the same time, product bioparticle 11 loadings in the MFB bioreactor 10 decreased significantly. These results support the hypothesis that loss of agitation resulted in poor gas-liquid mass transfer, depletion of oxygen in the medium, and poor soybean growth.

A second cause of poor growth after day 34 may be dilution of endogenous growth factors (Bramble, J., et al., Biotechnology progress 6:452–457 (1990)). During bioparticle removal on day 34, the soybean culture was found to be growing out of the bioparticle 11 at the bottom of the MFB bioreactor 10. Some bioparticle particles were connected by plant tissue, making the removal procedure difficult. Growth outside of the immobilization matrix also resulted in high medium turbidity. Between days 34 and 38, 2.4 L out of the approximately 3 L working liquid volume were exchanged with fresh medium to counter this problem. While soybean growth in the liquid phase was avoided, dilution of important plant hormones may have reduced growth rates.

Figure 3:
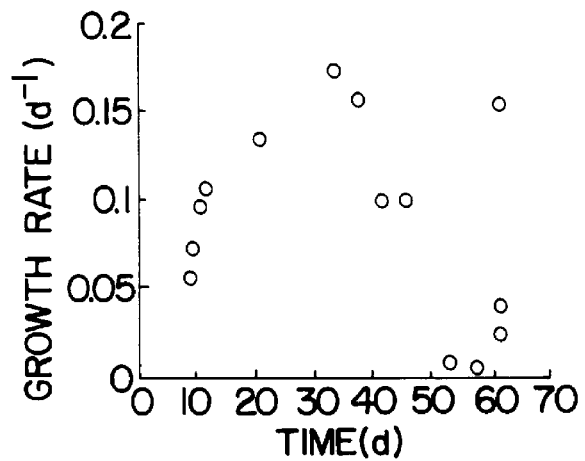
FIG. 3 is a graph showing soybean specific growth rate during MFB operation as a function of time in days (d).

FIG. 3 shows specific growth rates as a function of time. Growth rates mirror product bioparticle 11 densities as expected. With caution regarding uncertainties in residence time calculations, the MFB bioreactor 10 growth rates can be compared to batch shake flask cultures of immobilized soybean. The peak MFB value of 0.17 day$^{-1}$ compares well to the shake flask value of 0.26 day$^{-1}$. The average MFB bioreactor 10 growth rate is roughly one-third of that in shake flask culture. Furthermore, at least part of the lower growth rates can be explained by stress due to the antibiotic cocktail used in the MFB bioreactor 10, as illustrated by batch shake flask studies. Growth rates fell to their lowest values after day 50, but showed a rebound in the bioparticle 11 removed on the last day of operation.

Presaturation of the Liquid Phase. Calculation of dissolved oxygen concentration as a function of column height indicates presaturation was satisfactory for the experimental conditions. The oxygen consumption rate (Q) was calculated from the measured suspension culture respiration rate of 28 mg $O_2$/g cells-hr, and an integral average cell density of 3.0 g/L. The average density was based on feed and product bioparticle 11 densities of 0.4 and 10 g/L respectively. For these conditions, the dissolved oxygen would be depleted by 4.7% across the length of the column. If mass transfer resistances in the bioparticle 11 or between the bioparticle 11 and liquid were significant, this number would be even lower.

Respiration and Oxygen Diffusion. Thiele modulus calculations suggested that soybean respiration was not rate limited by oxygen diffusion in the bioparticle 11. In all respiration measurements, the oxygen-uptake rates were found to be independent of dissolved oxygen concentration. The respiration rate of soybean in MFB bioreactor 10 product bioparticle 11 was measured at 8.9 mg $O_2$/g cells-hr. The observed volumetric rate was $2.9 \times 10^{-9}$ g $O_2$/mL bioparticle-sec yielding an observable modulus of 0.02. A graphical solution of $\eta$ as a function of $\Phi$ is available for Michaelis-Menton kinetics in the zero-order regime (Bailey, J., and D. Ollis, Biochemical engineering fundamentals. McGraw-hill: New York (1986)). The resulting effectiveness factor of 1.0 indicates that oxygen diffusion within the bioparticle 11 is not rate limiting. The immobilized bioparticle 11 respiration rate was roughly one-third of that for suspension culture in exponential growth phase, 28 mg $O_2$/g cells-hr. The difference is consistent with the growth rate of the immobilized culture being approximately 0.1 day$^{-1}$ (roughly one-third of suspension culture). Furthermore, the immobilized soybean residence time was approximately 16 days. The respiration rate of a post-exponential phase suspension culture (19 days old) was 8.7 mg $O_2$/g cells-hr, which is very close to that of the immobilized soybean culture.

Figure 4A:
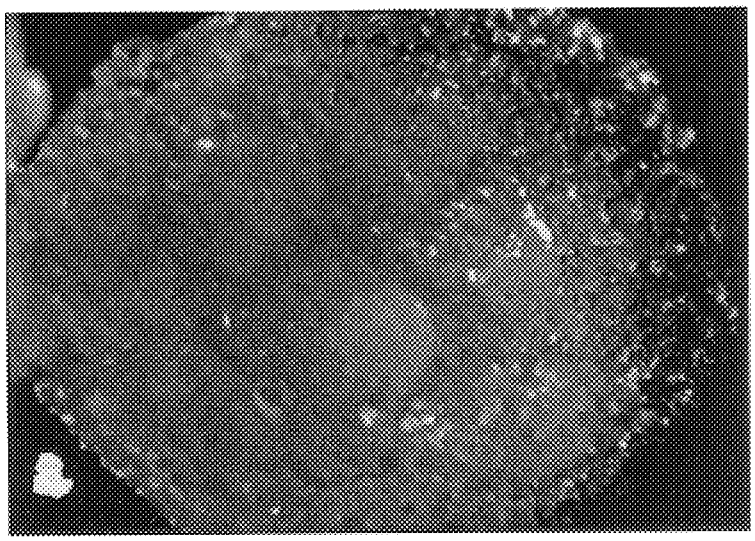
FIGS. 4A to 4C are photographs showing MFB product bioparticle cross-sections at 40 times magnification.
Figure 4B:
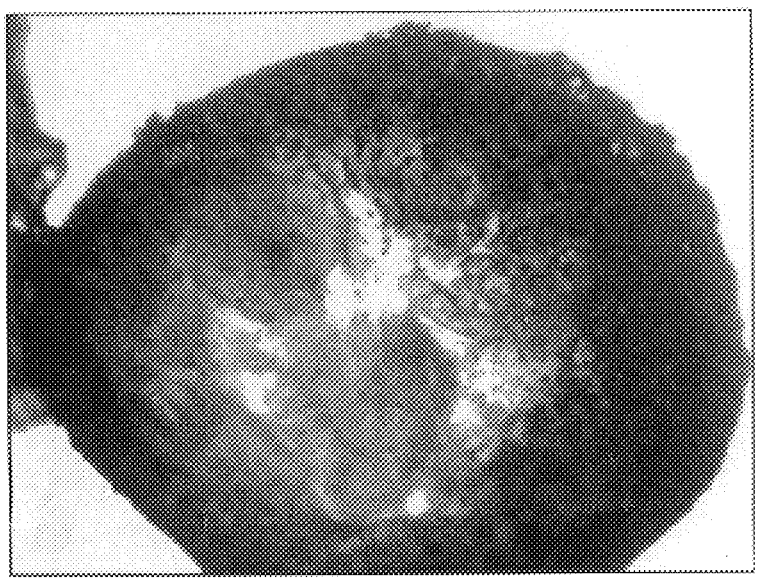
Figure 4C:
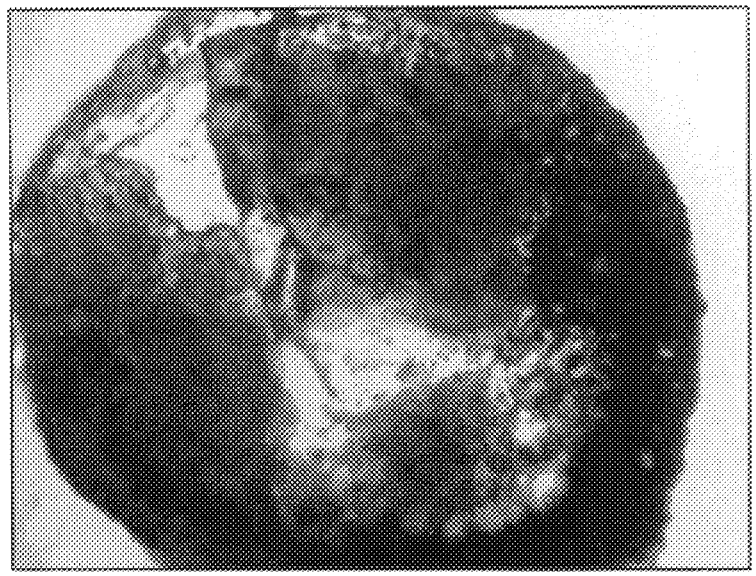

Microscopy of product bioparticle 11 cross-sections supported the idea that oxygen diffusion was not rate limiting. Example pictures of bioparticle cross-sections are shown in FIGS. 4A, 4B and 4C. No radial dependence of cell concentration was observed. Soybean aggregates appeared to be randomly distributed throughout the bioparticle, as opposed to preferentially located near the bioparticle 11 surface. The latter trend was observed by Bramble et al. (Bramble, J., et al., Biotechnology Progress 6:452–457 (1990)) with *C. arabica* in 3–4 mm alginate beads. Images from days 38, 42, and 62 showed soybean aggregates to be large relative to suspension culture. Aggregates up to 1 mm across were seen, with aggregates from 0.1 to 0.5 mm being most common. The general observation of large and dispersed aggregates may be explained by immobilization technique and hormone dependent growth. Large aggregates are expected to develop from inoculum aggregates which are above some minimum size. Growth of such aggregates may be explained by the feeder and dividing aggregate model proposed by Shuler (Shuler, M., Ann. N. Y. Acad. Sci. 65–79 (1981)). Thus aggregates which started large may continue increasing in size while smaller ones grow poorly or not at all. Poorly growing aggregates may however, be bolstered if they are surrounded or engulfed by rapidly growing large aggregates. Furthermore, the somewhat dispersed nature of the soybean in the bioparticle suggests that higher inoculation densities would provide higher final densities for a given residence time. Higher inoculation densities could reduce the void volume observed in the cross-section images.

While intra bioparticle 11 oxygen diffusion does not appear to be rate limiting, oxygen diffusion within soybean aggregates may be important. Modulus values for typically observed aggregates (0.1 to 0.5 mm diameter) range from 0.5 to 2.3. Based on a modulus of 1.0, rate limitation due to oxygen diffusion would be expected for aggregates larger than 0.2 mm. For zero order kinetics where $\phi$ is greater than unity, $\eta$ is equal to $\phi^{-1}$ (Froment, G., and Bischoff, K., Chemical Reactor Analysis and Design. John Wiley & Sons: New York (1979)). The effectiveness factor for 0.5 mm aggregates is therefore 0.4. For the largest aggregates observed (roughly 1 mm), the calculated effectiveness factor is 0.2. These results indicate that soybean aggregates may become diffusion limited as they move through the MFB bioreactor 10. However, Ananta et al. (Ananta, M., et al., Biotech. Bioeng. 47:541–549 (1995)) have found that experimental results do not agree with Thiele modulus calculations. Aggregates ranging from 3.0 to 12.5 mm in diameter were capable of active growth and respiration with retention of cell viability in at least 90% of the particle; observed specific oxygen uptake rates were within the range normally associated with plant cell suspensions. It is therefore unclear whether oxygen diffusion limits growth rates inside soybean aggregates.

Figure 5:
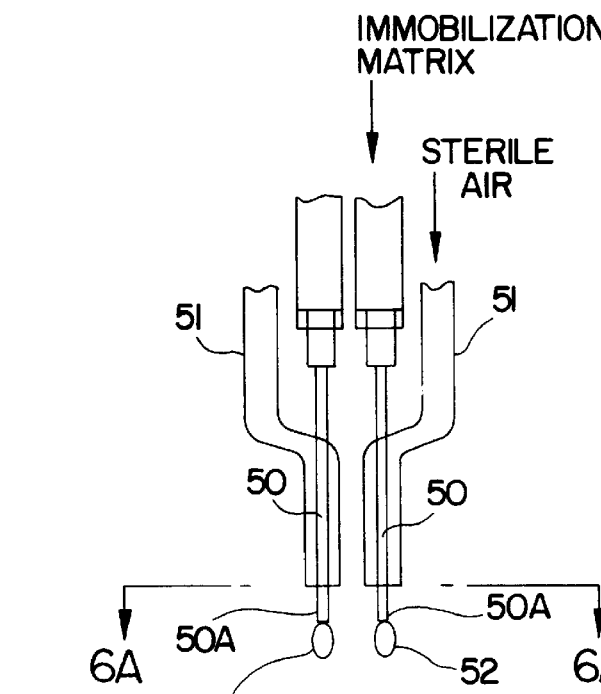
FIG. 5 is a graph showing isoflavonoid content in parts per million (ppm) of product soybean on a weight per dry weight basis as a function of time in days.
Figure 5:
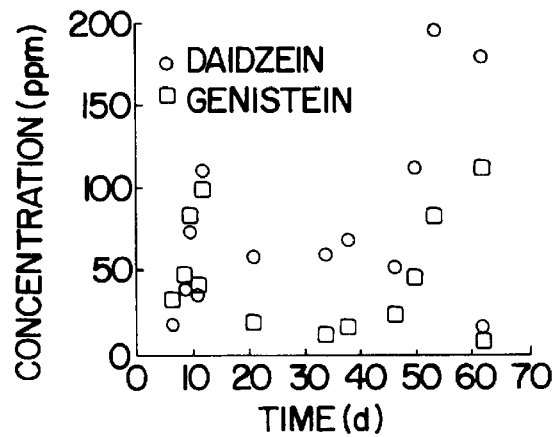

Isoflavonoid Production. Daidzein and genistein were produced during the entire run with concentrations ranging from approximately 10 to 200 $\mu$g per gram of dry soybean tissue. The daidzein and genistein concentrations are shown as a function of time in FIG. 5. The data are for hydrolyzed extracts, representing the total genistein or daidzein found in the soybean as both free isoflavonoid and isoflavonoid with moieties. Acid hydrolyzed extracts averaged nearly 2.9 and 1.5 times the amount of daidzein and genistein respectively in raw extracts. Thus nearly two-thirds of the daidzein and one-third of the genistein exists with sugar moieties. The extraction protocol was also tested using two week old soybean suspension cultures, providing isoflavonoid concentrations for comparison. Concentrations were 340±50 ppm and 560±160 ppm at a 95% confidence level for daidzein and genistein respectively. Daidzein concentrations in the MFB bioreactor 10 reached over one-half the average suspension culture level. Genistein concentrations reached nearly one-fifth the average suspension culture level. While peak isoflavonoid levels in the MFB bioreactor 10 were significantly below suspension culture values, the results are for the first continuous run attempted. Improved operating procedures and process control can reasonably be expected to raise the product concentrations considerably.

System Improvements. The two month, continuous run demonstrated the feasibility of continuous production of plant secondary metabolites in an MFB bioreactor 10. It also identified potential improvements in the experimental protocols that could yield steady-state operation.

Future experiments can benefit from automatic control of the dissolved oxygen concentration. A gas recycle loop can maintain good mass transfer between the gas and liquid while minimizing stripping of volatiles that may regulate the metabolism of the cells. A controller can be used to adjust the total gas flow rate (fresh air) to match the oxygen demand. A high recycle gas flow rate and impeller speed should be able to maintain a high gas-liquid mass transfer coefficient independent of the total gas flow rate. This can avoid volatiles stripping by excessive total gas flow rates typically used to maintain reasonable gas-liquid mass transfer.

Liquid medium 22 was added/removed along with bioparticle 11 addition/removal. For tighter control of net liquid medium 22 flow, fresh medium reservoir 37 can be continually added to the mixing vessel 17, and removed via gravity through an overflow port (not shown). Improved solids metering during addition and removal can be achieved by use of graduated tubing for bioparticle volume measurements. Evacuation of air from the bioparticle 11 outlet tubing 25 can avoid large air bubbles rising through and disrupting the bioparticles 11. Improved metering and decreased bioparticle 11 mixing can in turn lead to tighter residence time control.

Conclusions

Continuous isoflavonoid production from soybean with bioparticle throughput has been demonstrated in a MFB bioreactor 10 for over 2 months. Immobilization of soybean cell culture in alginate with stainless steel particles reduced the specific growth rate about 25% relative to suspension culture. Soybean growth rates and product concentrations were lower in the MFB bioreactor 10 than batch suspension cultures. Genistein and daidzein production ranged from 10 to 200 $\mu$g per gram of dry soybean tissue. Hydrolysis of bound daidzein and genistein was found to be important for product recovery. Both Thiele modulus calculations and bioparticle microscopy suggested that intra-bioparticle oxygen diffusion was not rate limiting. Ampicillin, Timentin, and Benlate had limited phytotoxicity at concentrations useful in preventing contamination during long, continuous bioreactor 10 operation.

It is intended that the foregoing description be only illustrative of the present invention and that the present invention be limited only by the hereinafter appended claims.

We claim:

1. In a continuous process for growing plant cells in a culture medium and removing the cells from the culture medium, the improvement which comprises:
   (a) providing bioparticles, formed by binding the cells of the plant material and magnetically susceptible particles together, in a column with opposed ends for inlet and outlet of bioparticles and with an activated first electromagnetic field generator around the column between the ends which produces a magnetic field which holds the bioparticles in position in a portion of the column without mixing of the bioparticles in the column and with an activated second electromagnetic field generator around the column acting with a magnetically susceptible screen across the column as a magnetic valve to prevent bioparticles from being moved from the portion of the column between the first electromagnetic field generator and the outlet;
   (b) circulating a culture medium for the cells through the bioparticles as they are held in position by the activated electromagnet; and
   (c) repeatedly adding bioparticles at one part of the column; and
   (d) removing bioparticles from another part separated from the one part of the column by inactivating the second electromagnetic field generator, without inactivating the first electromagnetic field generator, wherein a portion of the bioparticles are removed from the magnetic field.

2. The process of claim 1 wherein the plant cells are soybean.

3. The process of claim 1 wherein the plant cells are soybean which contain an isoflavonoid.

4. The process of claim 3 wherein the isoflavonoid is selected from the group consisting of genistein, daidzein and sugar derivatives and mixtures thereof.

5. The process of claim 1 wherein a gel is used to bind the particles and plant cells together.

6. The process of claim 5 wherein the gel is alginate and wherein the gel upon formation contains a liquid growth media for the cells.

7. The process of claim 6 wherein the bioparticle is a bead of the gel, plant cells and magnetically susceptible particles which is formed at a tip of a needle and removed with a sterilized gas stream into a hardening solution of a salt which is non-toxic to the plant cells.

8. The process of claim 7 wherein the magnetically susceptible particles are stainless steel.

9. The process of claim 1 wherein the column is vertically oriented, wherein the inlet end of the column is an upper part where the bioparticles are added and wherein the outlet end of the column is a lower part where the particles are removed.

10. The process of claim 9 wherein the culture medium is circulated from the outlet of the column to the inlet end of the column for the bioparticles.

11. The process of claim 1 wherein gas bubbles are added to the circulating culture medium.

12. The process of claim 11 wherein the bubbles are air.

13. The process of claim 1 wherein the addition of the bioparticles to the column is continuous.

14. The process of claim 1 wherein in addition a chemical is separated from the cells.

15. The method of claim 1 wherein after step (d) a chemical in the cells is separated which includes a sugar moiety which is hydrolyzed from the chemical in a hydrolysate and then the chemical as hydrolyzed is separated from the hydrolysate.

* * * * *